United States Patent [19]
Bryant et al.

[11] Patent Number: 5,234,419
[45] Date of Patent: Aug. 10, 1993

[54] SUCTION DRAINAGE INFECTION CONTROL SYSTEM

[75] Inventors: Peter L. Bryant, Lake Forest; Richard W. Grabenkort, Barrington; James F. Middaugh, Deerfield; Timothy J. Oswald, Lincolnshire; Edward S. Tripp, Park City, all of Ill.

[73] Assignee: Abbott Laboratories, Abbott Park, Ill.

[21] Appl. No.: 906,015

[22] Filed: Jun. 26, 1992

Related U.S. Application Data

[63] Continuation of Ser. No. 457,908, Dec. 27, 1989, abandoned, which is a continuation-in-part of Ser. No. 330,552, Mar. 30, 1989, abandoned.

[51] Int. Cl.$^5$ .............................................. A61M 1/00
[52] U.S. Cl. ................................... 604/320; 604/321; 604/319; 604/318; 604/87; 604/89; 137/205; 137/432; 141/65
[58] Field of Search ............... 137/205, 208, 432, 433; 604/310–311, 91, 317–323, 35, 147; 141/65

[56] References Cited

U.S. PATENT DOCUMENTS

| | | | |
|---|---|---|---|
| 3,312,221 | 4/1967 | Overment | 604/333 X |
| 3,324,855 | 6/1967 | Heimlich | 604/3 |
| 3,466,131 | 9/1969 | Arcudi | 604/310 X |
| 3,507,282 | 4/1970 | Burding | 604/333 |
| 3,727,788 | 4/1973 | Holbrook | 604/319 X |
| 3,863,634 | 2/1975 | Reynolds et al. | 604/320 X |
| 3,938,540 | 2/1976 | Holbrook et al. | 137/205 |
| 3,982,538 | 9/1976 | Sharpe | 137/197 X |
| 4,384,580 | 5/1983 | Leviton | 604/319 X |
| 4,505,703 | 3/1985 | Gale et al. | 604/317 |
| 4,529,398 | 7/1985 | Wong et al. | 604/322 X |
| 4,661,100 | 4/1987 | Rechsteiner | 604/317 X |
| 4,681,571 | 7/1987 | Nehring | 137/205 X |
| 4,693,712 | 9/1987 | Bates | 604/323 |
| 4,855,064 | 8/1989 | Schlein | 604/83 X |

FOREIGN PATENT DOCUMENTS

| | | | |
|---|---|---|---|
| 0941700 | 2/1974 | Canada | 604/321 |
| 8700439 | 1/1987 | World Int. Prop. O. | 604/319 |

Primary Examiner—Randall L. Green
Assistant Examiner—D. Willse
Attorney, Agent, or Firm—Thomas M. Breininger; A. Nicholas Trausch

[57] ABSTRACT

A suction drainage control system that reduces an operator's exposure to infectious waste by permitting waste-treating material to be dispersed into a sealed chamber in which the infectious waste is contained. The sealed chamber includes a cover with a flexible liner sealed to and suspended therefrom. A freely movable reservoir is provided inside the sealed chamber for storing the waste-treating material, which reservoir is opened by manipulating the flexible liner to open the reservoir.

14 Claims, 6 Drawing Sheets

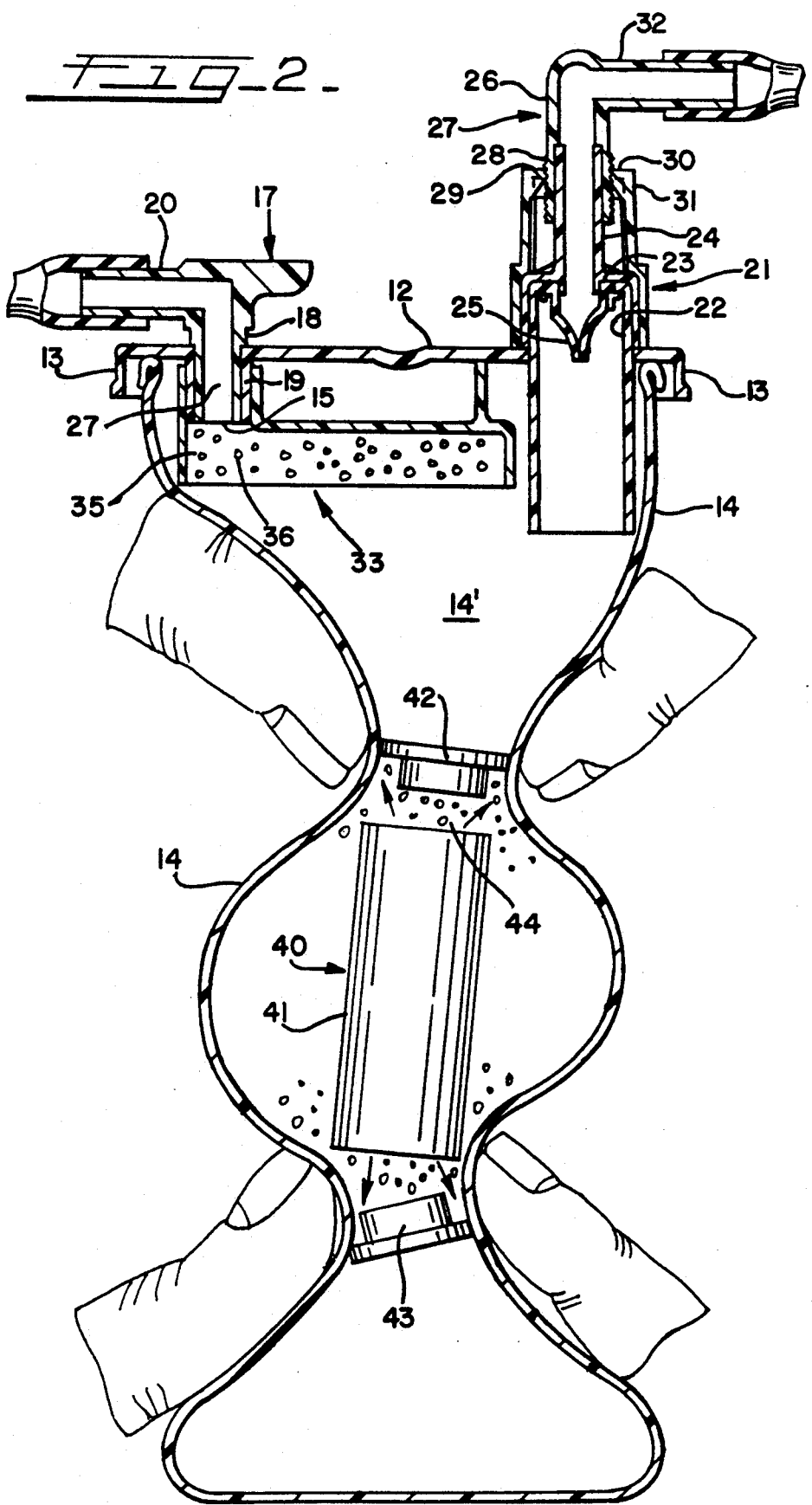

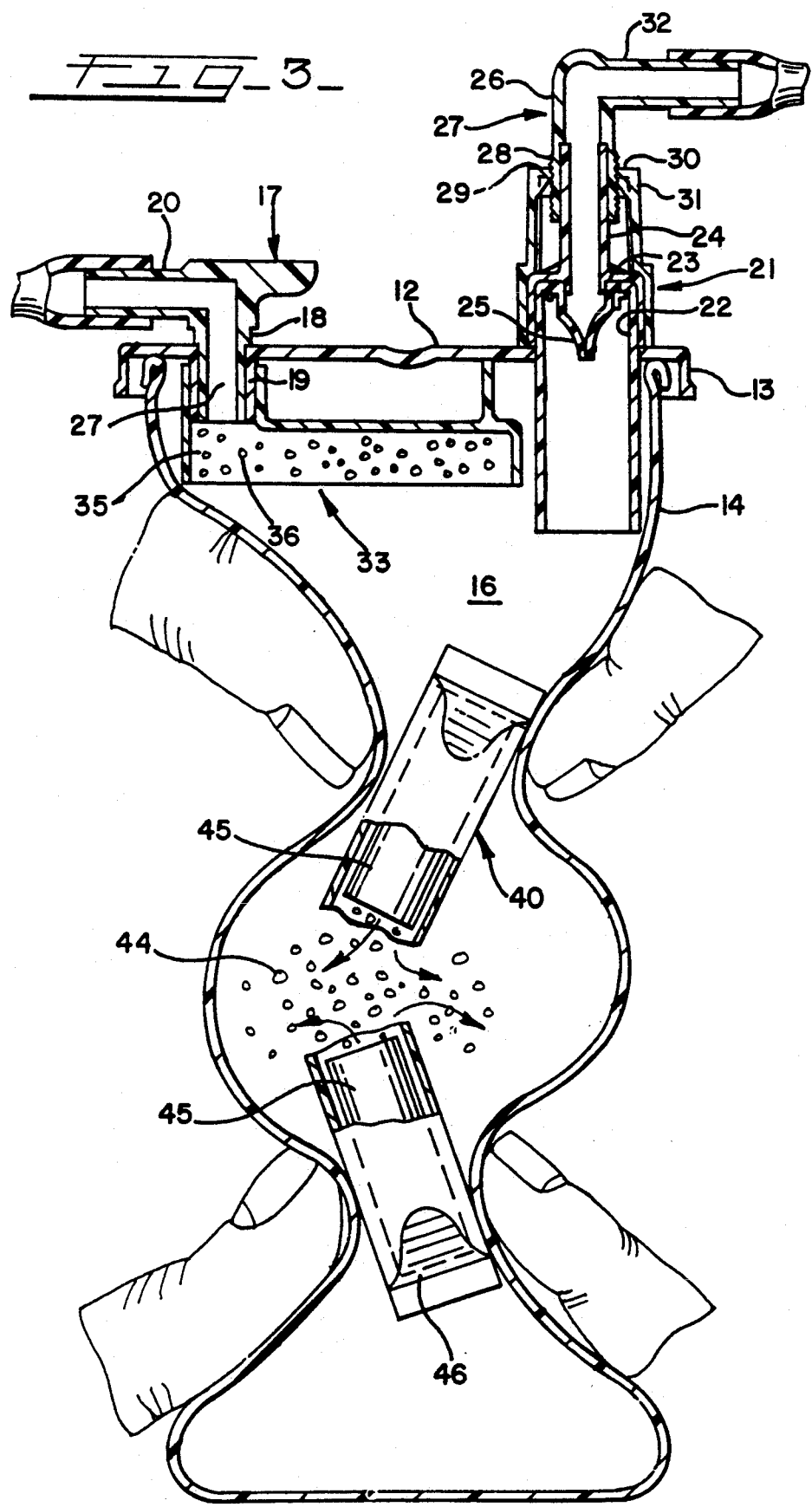

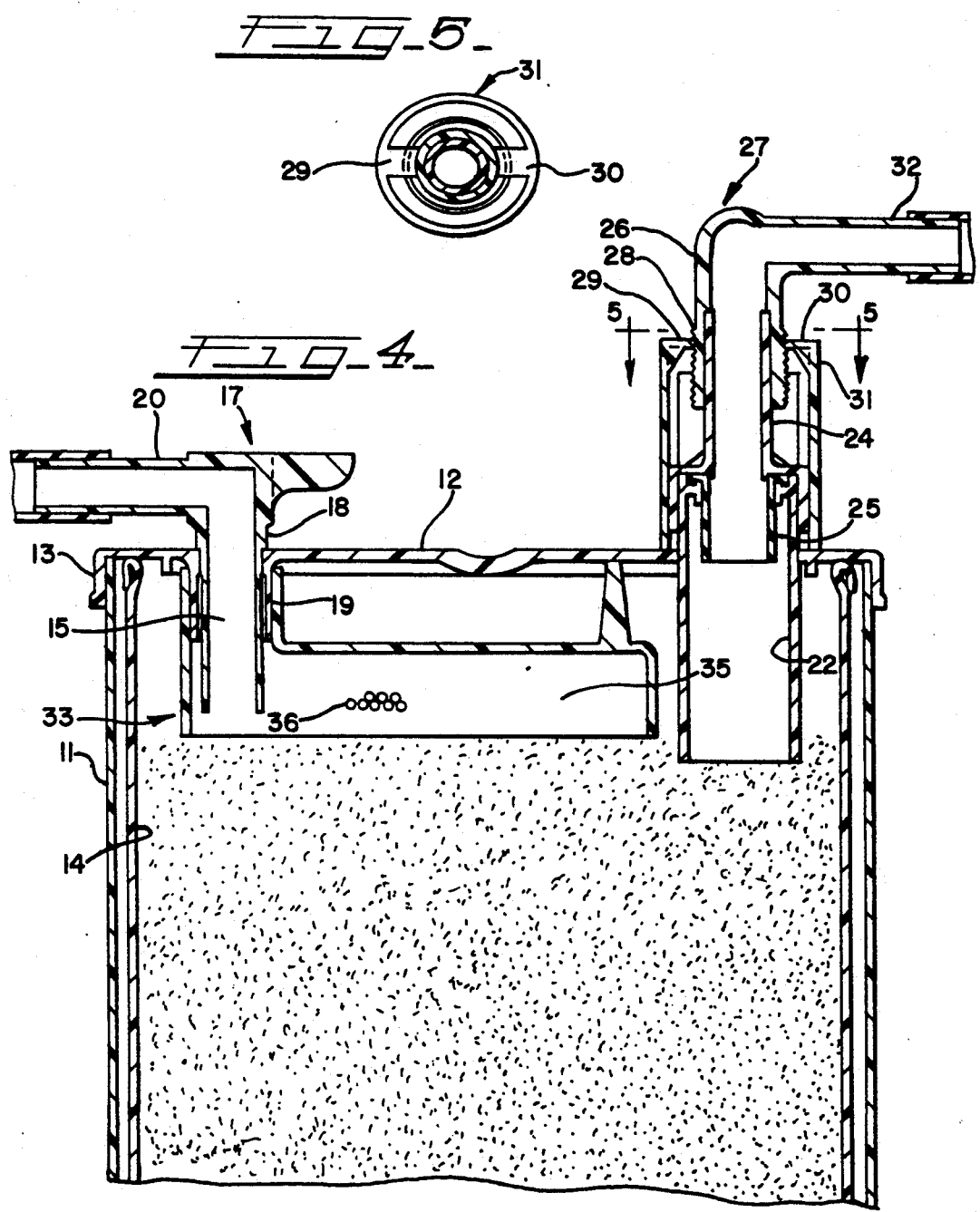

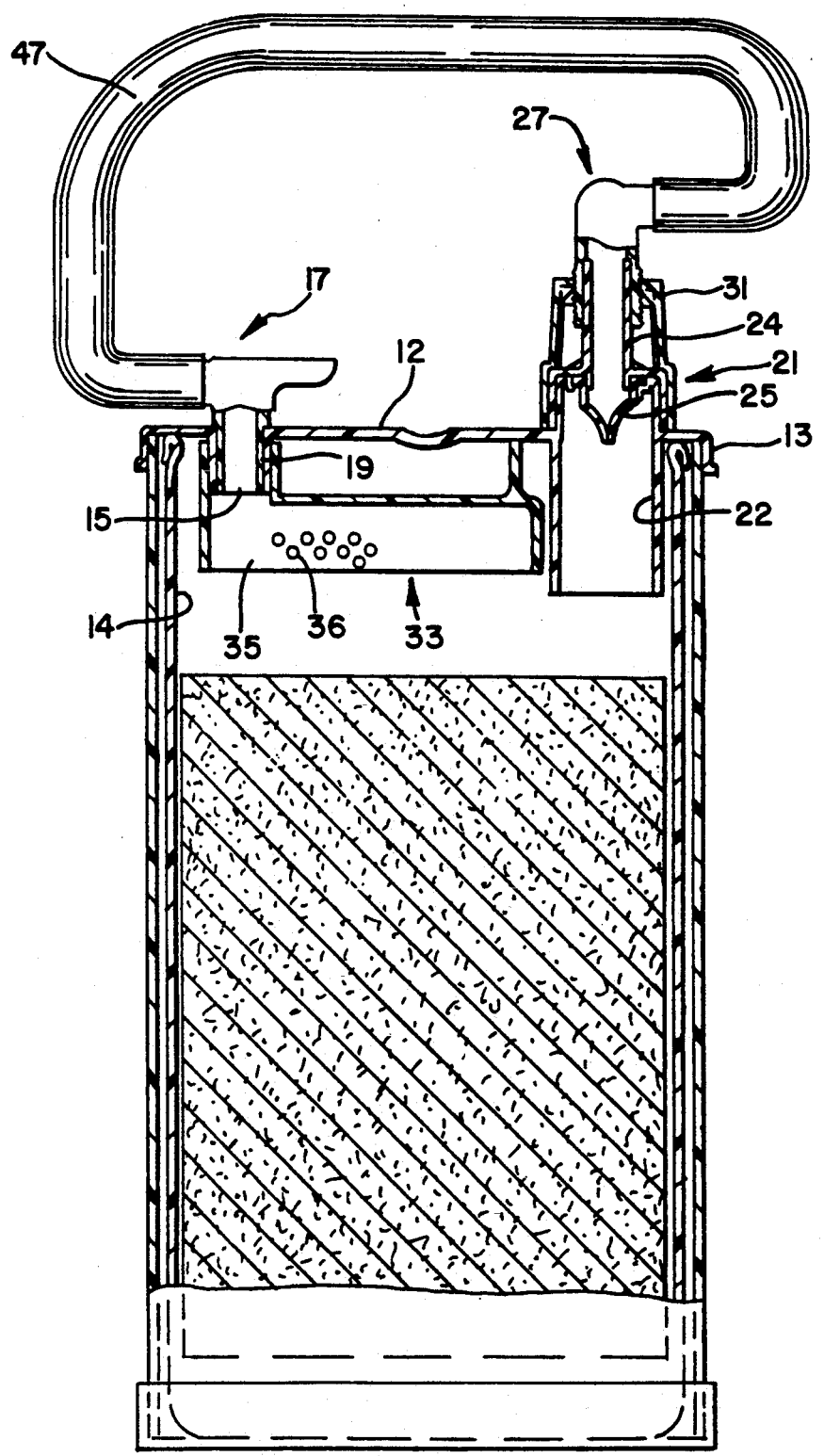

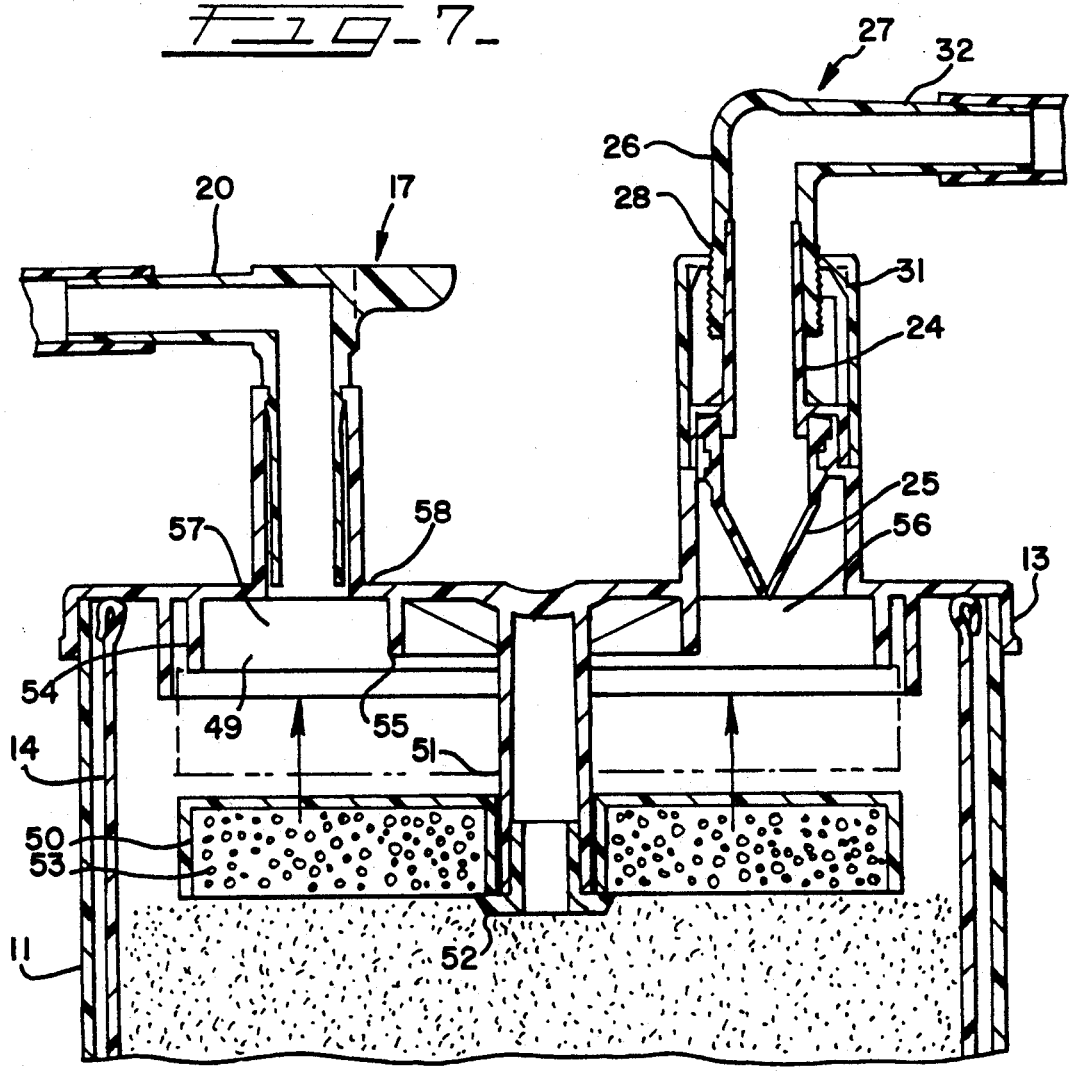
FIG_7_
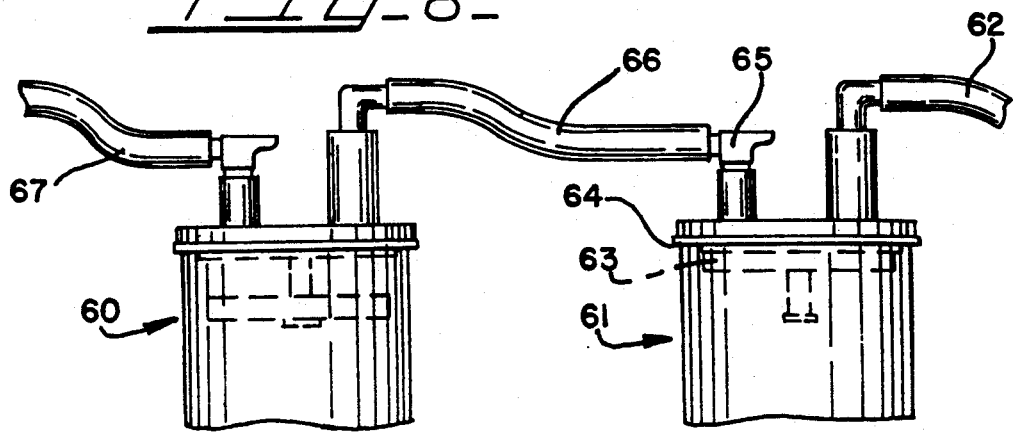
FIG_8_

SUCTION DRAINAGE INFECTION CONTROL SYSTEM

This application is a continuation of application Ser. No. 07/457,908, filed Dec. 27, 1989, now abandoned, which is a continuation-in-part of application Ser. No. 07/330,552, filed Mar. 30, 1989, now abandoned.

BACKGROUND OF THE INVENTION

Suction drainage systems having a connection from a rigid container or a flexible liner to the body of a patient and a connection from the container or liner to a suction source have been widely utilized in hospitals. These systems collect waste from surgical and other patients in a disposable container or flexible liner having an integral lid or cover. The waste being collected often is highly infectious and is often subject to exposure caused by spills or a failure of the suction drainage system.

Accordingly, it is an object of the present invention to provide a suction drainage container infection control system.

It is a further object of the present invention to provide a suction drainage infection control system incorporating an enclosed reservoir containing a waste treating material, such as a germicide and/or absorbent disposed within a reservoir that can be opened to empty its contents when desired, and/or improved valves and/or a transfer system and/or locking features in the lid to minimize the escape of fluid after capture.

SUMMARY OF THE INVENTION

The present invention is directed to a suction drainage infection control system.

More particularly, the present invention is directed to a suction drainage infection control system wherein waste-treating material is released into a flexible and sealed liner or bag in which infectious or contaminated waste is collected.

This invention is also directed to a suction drainage infection control system having improved valves, a multi-container transfer system and locking features in the lid of the flexible liner.

The suction drainage infection control system of the present invention can include means for chemically treating the waste and/or means for capturing and transferring the waste in a solid or semi-solid state. Each suction drainage canister may be used alone or in series with one or more additional canisters.

The suction drainage infection control system of the present invention minimizes the risk of exposure for hospital personnel to infectious waste by decreasing the risk of infection and spills caused by failure to cap off full or partially full waste containers, accidental cap disconnection and liner breakage.

The suction drainage infection control system of the present invention promotes the safe handling of potentially infectious suction waste by exposing the collected waste to an effective germicidal agent that is capable of killing many types of bacteria and viruses at room temperature. The germicide is effective against HIV, hepatitis B, herpes, simplex I, polio, adeno virus, and many other potentially infectious materials, and thus dramatically reduces the potential of crosscontamination between patients and minimizes the associated risk to health care workers.

In a preferred form, the chamber includes a unitary structure comprising the flexible liner or bag which is suspended from and sealed to a cover that defines a sealed area into which infectious or contaminated waste is drawn. To protect the bag during use, an open top canister may support and surround the bag and be releasably secured to the cover.

A normally closed, easily opened, freely movable enclosed reservoir which contains waste-treating material is disposed within the sealed chamber. Release of the waste-treating material into the sealed chamber is effected by having the operator manipulate or collapse the flexible liner sufficiently to open the reservoir to permit the waste-treating material to be released into the chamber. In one embodiment, end caps are provided on the reservoir that may be made of a material that allows it to float once they are removed from the reservoir. The ability of the cap to float provides a visual indicator that the system has been activated.

An inlet port located in the cover of the sealed chamber leads from the source of waste to the sealed chamber. An outlet port in the cover leads from the sealed chamber to a suction source. After the reservoir has been opened, the waste flowing into the chamber mixes with and disperses the waste-treating material.

To inhibit the waste from escaping the sealed chamber, the inlet port preferably includes a valve which provides one-way flow of waste from its source into the sealed chamber. The waste-treating material can be either a germicide which chemically treats the waste and/or an absorbent which allows capture and transfer of the waste in a solid or semi-solid state. When the reservoir is opened, the waste-treating material is freely dispersed into the contents of the sealed chamber.

The system of the present invention simplifies the process by which infectious waste is treated for further disposal and handling. Moreover, the aseptic drainage control system of the present invention minimizes the risk of exposure for hospital personnel to infectious waste by treating such waste within a sealed chamber.

The present invention will best be understood by reference to the following specification and claims taken in conjunction with the accompanying drawings, in which:

BRIEF DESCRIPTION OF THE DRAWINGS

FIG. 2 is a vertical section of the embodiment of FIG. 1 illustrating the manipulating of the liner to open the reservoir containing the germicide and/or absorbent composition for treating and/or solidifying the waste;

FIG. 3 is a vertical section of a second embodiment of the present invention;

FIG. 4 is a fragmentary vertical section of a single canister in which the waste treating material has been dispersed;

FIG. 5 is a sectional view taken substantially as indicated by the line 5—5 of FIG. 4;

FIG. 6 is a vertical section of the embodiment of FIG. 1 after the liner is full and the germicide and/or absorbent composition has treated and/or solidified the waste;

FIG. 7 is a fragmentary vertical section of an embodiment of the present invention that is adapted for use with two or more canisters connected in series; and FIG. 8 is a view of two canisters of the present invention connected in series.

DETAILED DESCRIPTION OF THE PREFERRED EMBODIMENTS

Figure 1:
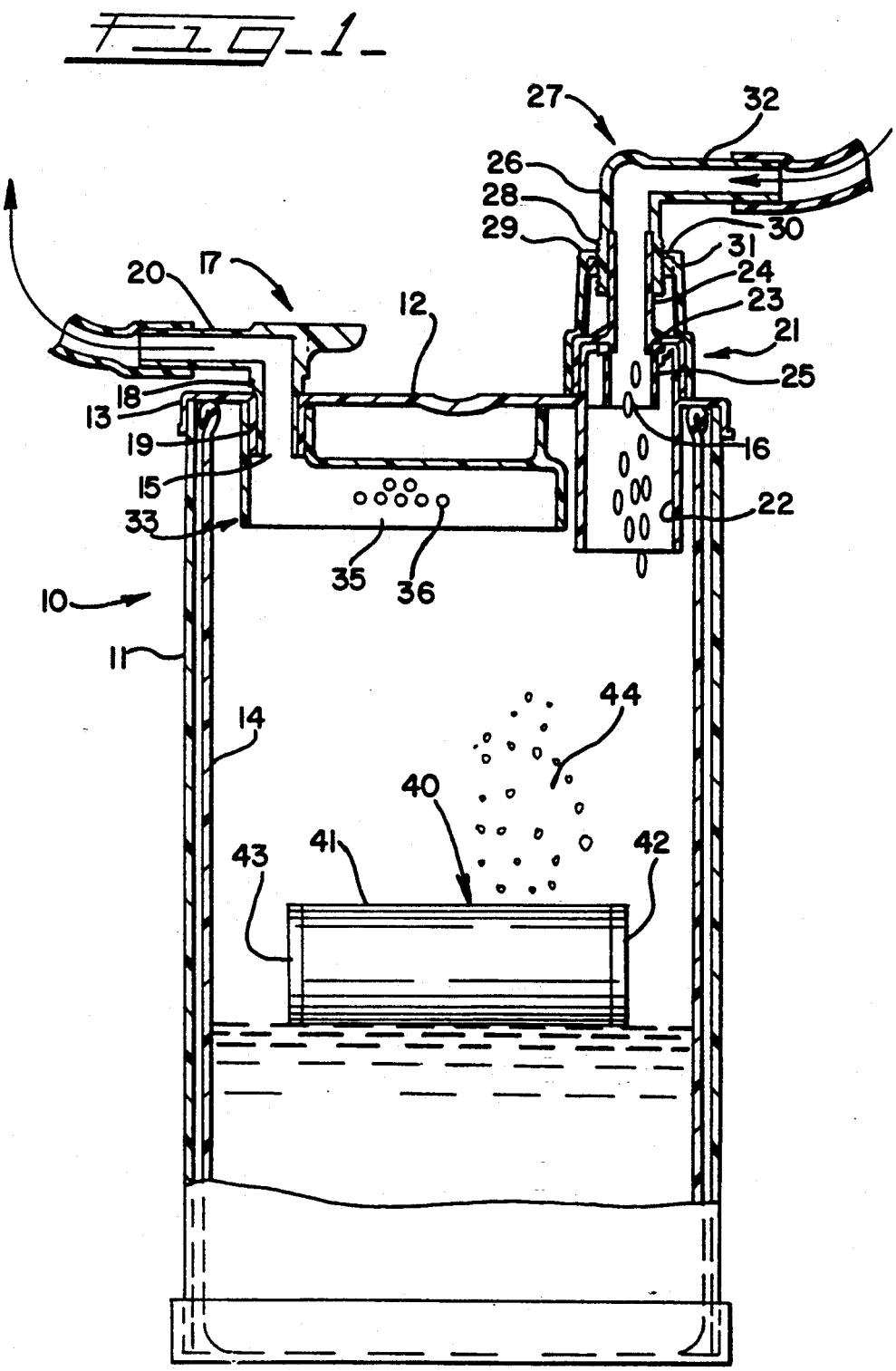
FIG. 1 is a vertical section of a first embodiment of the present invention while waste fluid is being drawn into the liner.

While the present invention is susceptible of embodiment in many forms, there is shown in the drawings and will hereinafter be described two presently preferred embodiments with the understanding that the present specification sets forth exemplifications of the invention, which are not intended to limit the invention to the specific embodiments illustrated.

Referring to the drawings, FIG. 1 is a vertical section of a first embodiment of the suction drainage container infection control system 10 of the present invention. The system 10 includes a cylindrical canister 11 that can be constructed of a relatively rigid plastic material and is open at the top and closed at the bottom. The canister itself is not contacted by the waste so it may be repeatedly used.

The canister 11 is adapted to receive a unitary structure comprising a canister lid 12 having a depending flange 13 for airtight engagement with the upper open end of the canister 11. Fused or otherwise secured to the underside of the lid 12 in a completely air-tight manner is a flexible liner 14. The lid 12 is preferably constructed from a relatively rigid plastic material, while the liner 14 is preferably constructed from a flexible thermoplastic material. Extending through the lid 12 are openings 15 and 16. Opening 15 contains a fitting 17 with a depending portion 18 which engages a depending flange 19 from the lid 12 in an airtight manner. The fitting 17 also includes an upper portion 20 that is adapted to be connected to a suction line (not shown).

A fitting 21 is inserted in opening 16 in an airtight manner. Fitting 21 includes a depending tubular portion 22 that extends above and below the surface of the lid 12 and helps to direct the incoming waste toward the bottom of the liner 14. Fitting 21 also has a shoulder 23 that supports a tubular upper portion 24 and a one-way double slit "duckbill" valve 25 that permits flow of waste into the liner 14 while preventing escape of waste from the liner. Other suitable duckbill valves are disclosed in U.S. Pat. Nos. 3,822,720 and 3,901,272. The lower portion 26 of elbow 27 fits over upper arm 24. The lower portion 26 of elbow 27 has teeth 28 that are rotatably and/or straight push engaged by flanges 29 and 30 of a collar 31 that is engaged at its lower end by fitting 21. This secures elbow 27 to lid 12. Elbow 27 may be removed from the lid 12 by squeezing and/or rotating the upper portions of collar 31 that are between flanges 29 and 30.

A nonmechanical valve 33 is mounted in the lid 12. The nonmechanical valve 33 comprises a housing 34 that contains a polyethylene foam 35 containing swellable moisture sensitive particles 36 made of polymers or other suitable materials. A suitable nonmechanical valve is disclosed in published PCT application No. WO 87/00439. This valve permits normal air flow through suction opening 15 until it becomes wet, whereupon the polymer particles swell to block air and waste flow.

As shown in FIG. 1 and FIG. 2, the lid 12 and liner 14 form a sealed chamber 14' which contains a normally closed reservoir generally indicated by reference numeral 40, which stores a waste-treating material therewithin as long as the reservoir 40 remains closed. The reservoir is made of a hollow plastic tube 41 that is closed at its ends by end caps 42,43. Located within the tube is a waste treating material, such as a germicide and/or absorbent 44.

In the embodiment illustrated in FIG. 3, the reservoir 40 consists of a split tube 45 that is filled with a waste-treating material such as a germicide and/or an absorbent 44 and is enclosed by a sealed wrapper 46. The tube can be in abutting relationship or telescoped as long as it can be readily opened when the outer wrapper that is made of a material such as paper that can be easily opened is opened by ripping or tearing.

The waste-treating material is dispersed into the sealed chamber 14'. As used herein, the terms "dispersed" or "dispersion" are intended to include the release of waste-treating material into the sealed chamber 14'.

The waste-treating material may be a powder or liquid and preferably comprises a germicide such as chlorine and/or an absorbent such as starch grafted acrylic polymer or any other suitable absorbent material. The germicide and/or absorbent will treat contaminants contained in the waste. In a preferred embodiment, the absorbent is of a type that will swell in size upon dispersion into the waste.

Representative suitable germicides include calcium hypochlorite, chlorinated trisodium phosphate, N-chlorosuccinimide, 1,3-dichloro-5,5-dimethylhydantoin, potassium dichloro-s-triazinetrione, sodium benzenesulfonchloramide, sodium hypochlorite, sodium p-toluenesulfonchloramide, sodium dichloroisocyanurate,dihydrate, sodium dichloro-s-triazinetrione, p-sulfondichlor-amidobenzoic acid, p-toluenesulfon-dichloramide, trichloroisocyanuric acid, trichloromelamine, alcohols, fomaldehyde, glutaraldehyde, hydrogen peroxide, iodines, quaternay ammonium compounds, paracetic acid, paraformaldehyde, and phenols. Preferred germicides include 1,3-dichloro-5,5-dimethylhydantoin, potassium dichloro-s-triazinetrione, N-chlorosuccinimide, and sodium dichloroisocyanurate dihydrate.

Representative suitable absorbents include cellulose fiber, cross-linked polymeric salts, diatomaceous earth, dried clay, expanded silicate particulates, ground corncobs, perlite, silica gel, shredded polypropylene microfibers, sodium/calcium borosilicate glass, starch grafted sodium polyacrylate, thermally reticulated polyether polyurethane, and vermiculite.

Dispersion or release of the waste-treating material into the sealed chamber 14' may be simply effected by collapsing the liner 14 and ripping open the wrapper and opening the tube of FIG. 3, or having an operator collapse the liner 14 and remove the end caps from the tube of FIG. 2.

During operation, a negative pressure or suction is introduced into the sealed chamber 14' as by connecting the vacuum or suction line 29 extending from the vacuum source to the suction fitting 17. When a suction or negative pressure is created in the sealed chamber 14', a positive pressure differential is developed on opposite sides of valve 25. The suction or negative pressure created draws waste through the inlet port 22 in a manner forcing an expansion of the valve 25 to permit flow therethrough into the sealed chamber 14' wherein the waste is received and collected. The positive pressure differential allows the valve 25 to act as a one-way flow valve.

Before, while or after the liner is filled with waste, germicide and/or absorbent is released by opening the reservoir 40 by manipulation of the end caps 42, 43 through the liner 14. The germicide and/or absorbent will treat contaminants contained in the waste. The liner 14 can fill until the level of waste reaches nonmechanical valve 33. When the valve 33 becomes wet, the polymer particles swell to block air and waste flow out of the liner 14. With no vacuum being drawn through the liner, one-way valve 25 closes to prevent waste from flowing out of the liner through inlet opening 16.

FIG. 4 is a fragmentary vertical section of an embodiment of the present invention that is adapted for use with a single canister. As waste enters the system 10 through the upper portion 32 of elbow 27, it passes through a one-way duckbill valve 25 into the liner 14 in canister 11. As the liner 14 fills with waste, the germicide and absorbent are released and the waste is treated. When the waste reaches the level of nonmechanical valve 33, the moisture-sensitive polymer particles 36 swell and shuts off the suction pressure in the liner, which prevents any more waste from entering the system. The swollen polymer beads block air and waste flows out of the liner through opening 15 and the one-way duckbill valve 25 prevents waste from escaping out through opening 16.

An additional feature of the system of the sectional view taken substantially as indicated by the line 5—5 of FIG. 4. Collar 31 has a pair of opposing flanges 29 and 30 which engage the teeth on the elbow 27 to lock and retain the collar 31 on the fitting. Elbow 27 can be released by squeezing the opposing portions of collar 31 that are between flanges 29 and 30.

FIG. 6 is a vertical section of the embodiment of FIG. 1 after the liner 14 has been filled with waste and the germicide and absorbent have been released into the waste. The absorbent swells and, upon removal the filled liner is semi-rigid or rigid. This tends to minimize the possibility of accidental rupture of or spills from the liner. One-way valve 25 is shown in its normal closed position. Tube 47 is also used to provide additional security against the possibility of accidental spills by securing elbow 27 to fitting 21. The lid and associated liner 14 may then be removed and discarded.

FIG. 7 is a fragmentary vertical section of an embodiment of the present invention that is adapted for use with two or more canisters connected in series. In this embodiment, a float 50 is slidably mounted on post 51, which has a knob 52 at its lowermost portion to support the float in its lowermost position. The float 50 is packed with buoyant material 53 so that when the waste reaches a level in the liner 14 where it contacts the lower surface of the buoyant material 53 the float 50 rises until circular wall 54 is contacted by the upper surface of the float 50. Circular wall 54 forms with circular wall 55 that is shorter than wall 54 an annular channel 49 through which opening 56 communicates with opening 57. The float 50 thus prevents the flow of waste into the liner 14. However, as seen from the drawing, the suction in opening 51 is present in opening 56 through channel 49 to continue to draw in waste through valve 25. As a result of the suction, the waste will flow directly from inlet opening 56 to outlet opening 57 through circular channel 49 and below wall 55. As shown in FIG. 8, waste then can pass from one canister to another. This feature is referred to as the transfer system.

In FIG. 8, there is shown a first container 60 and second container 61. Flexible tubing 62 is connected to means (not shown) for withdrawing waste from a patient. Container 61 is full of waste and float 63 is in sealing engagement in cap 64 so that waste passes directly to outlet means 65 and through flexible tubing 66 to canister 60 by means of suction being applied through tubing 67.

Operation of the suction system of the present invention may be stopped at any desired time by disconnecting the suction source from the suction fitting 17 of the waste receptacle. Advantageously, since the liner 14 is sealed to cover 12, once the liner is filled, the cover 12 and liner 14 may be disposed of intact.

While the form of apparatus herein described constitutes preferred embodiments of the invention, it is to be understood that the invention is not limited to these precise forms of apparatus, and that changes may be made therein without departing from the scope of the invention that is defined in the appended claims.

What is claimed is:

1. A suction system for draining waste from a source, said suction system comprising:
   a sealed container including a lid and flexible liner;
   waste inlet means in said lid;
   means in said lid attached to a suction source;
   a freely movable reservoir wholly enclosed within said sealed container for storing waste-treating material wherein said reservoir consists of a hollow tube that is closed at both ends by end caps at least one of which is formed from a material which generally floats when disposed in a liquid to serve as a visual indicator of activation of the waste treating material,
   said end cap defining openable closure means for closing said reservoir until said closure means are manipulated through the flexible liner to open the reservoir to permit dispersion of the waste treating material into the sealed container.

2. A suction system as in claim 1 wherein the waste inlet means contains a one-way valve that permits waste to flow only into the container.

3. A suction system as in claim 2 wherein the one-way valve is a double slit duckbill valve.

4. A suction system as in claim 1 wherein a nonmechanical valve is disposed in flow line with said suction source which prevents suction from being applied when the valve is contacted by waste, said nonmechanical valve containing fluid swellable particles.

5. A suction system as in claim 1 wherein the waste inlet means is removably secured to the lid.

6. A suction system as in claim 1 wherein said flexible liner is disposable and is secured to said lid.

7. A suction system as in claim 1 wherein the reservoir contains a germicide.

8. A suction system as in claim 1 wherein the reservoir contains an absorbent.

9. A suction system for draining waste from a source that comprises:
   a container that comprises a canister that contains a flexible liner and a lid therefor to which the liner is secured;
   waste inlet means releasably secured to said lid and having a one-way valve that permits waste to flow only into said liner;
   means in said lid attached to a suction source;
   means in said lid to stop suction from being applied in the waste inlet means when the waste in the liner has reached a specified level;
   a freely movable reservoir wholly enclosed within said container for storing waste-treating material wherein said reservoir consists of a hollow tube that is closed at both ends by end caps at least one of which is formed from a material which generally floats when disposed in a liquid to serve as a visual indicator of activation of the waste creating material, said end caps defining openable closure means for closing said reservoir until said closure means are manipulated through the flexible liner to open the reservoir to permit dispersion of the waste treating material into the container.

10. A suction system as in claim 9 in which the means in said lid for stopping suction from being applied in the waste inlet means comprises a nonmechanical valve to close the means in said lid attached to a suction source.

11. A suction system as in claim 10 in which the nonmechanical valve consists of a housing containing polyethylene foam containing swellable moisture-sensitive particles.

12. A suction system for draining waste from a source that comprises:

a container and a lid therefor;

waste inlet means releasably secured to said lid and having a one-way valve that permits waste to flow only into said container;

means in said lid attached to a suction source to seal suction from collected waste in the container when the waste in the container has reached a specified level and transfer the suction and waste flow to additional containers that are connected thereto;

wherein said sealing means consists of a float in the container that is movably mounted to the lid, said lid and float being constructed and arranged to close off the suction and inlet means from the container when it reaches the specified level, but permit flow between said suction and inlet means; and a freely movable reservoir wholly enclosed within said container for storing waste-treating material, said reservoir having closure means.

13. A suction system for draining waste from a source that comprises: a container and a lid therefor; waste inlet means releasably secured to said lid and having a one-way valve that permits waste to flow into said container but not out of same; means in said lid attached to a suction source to seal suction from collected waste in the container when the waste in the container has reached a specified level and transfer the suction and waste flow to additional containers that are connected thereto; wherein said sealing means consists of a float in the container that is movably mounted to the lid, said lid and float being constructed and arranged to close off the suction and inlet means from the container when it reaches the specified level, but permit flow between said suction and inlet means; and tubular paper-like reservoir means closed at both ends and containing waste-treating material, said reservoir means being disposed within said container.

14. A suction system for draining waste from a source, said suction system comprising:

a sealed container including a lid and a flexible liner;

waste inlet means in said lid;

means in said lid attached to a suction source;

a freely movable reservoir wholly enclosed within said sealed container for storing waste-treating material wherein said reservoir consists of a split hollow tube that is enclosed by a wrapper that can be readily opened to empty its contents into the sealed container and defining openable closure means for closing said reservoir until said closure means are manipulated through the flexible liner to open the reservoir to permit dispersion of the waste treating material into the sealed container.

* * * * *